United States Patent [19]

Litt

[11] Patent Number: 4,980,461

[45] Date of Patent: Dec. 25, 1990

[54] DNA PROBE WHICH REVEALS A HYPERVARIABLE REGION ON HUMAN CHROMOSOME 2

[75] Inventor: Michael Litt, Portland, Oreg.

[73] Assignee: The State of Oregon acting by and through the State Board of Higher Education on behalf of Oregon Health Sciences University, Eugene, Oreg.

[21] Appl. No.: 54,760

[22] Filed: May 27, 1987

Related U.S. Application Data

[63] Continuation-in-part of Ser. No. 46,831, May 4, 1987, and a continuation-in-part of Ser. No. 53,320, May 22, 1987.

[51] Int. Cl.$^5$ .................. C07H 21/00; C12Q 1/68; G01N 33/48; G01N 33/53
[52] U.S. Cl. ........................... 536/27; 435/6; 435/172.3; 436/501; 935/9; 935/19; 935/23; 935/78; 935/79; 935/80
[58] Field of Search ............... 435/6, 172.3; 436/501; 536/27; 935/78, 9, 19, 23, 79, 80

[56] References Cited

U.S. PATENT DOCUMENTS

| | | |
|---|---|---|
| 4,302,204 | 11/1981 | Wahl et al. ............... 23/230.3 |
| 4,468,464 | 8/1984 | Cohen et al. ............... 435/317 |
| 4,594,318 | 6/1986 | Gusella et al. ............... 435/6 |
| 4,623,619 | 11/1986 | Owerbach et al. ............ 435/6 |

OTHER PUBLICATIONS

White, R. et al., (1986), in *DNA Probes, Applications in Genetic and Inf. Disease and Cancer,* (Ed. L. S. Lerman, Cold Spring Harbor Labs., Cold Spring Harbor, N.Y.), pp. 43–47.

Wyman et al., "A Highly Polymorphic Locus in Human DNA", *Proc. Natl. Acad. Sci., U.S.A.,* 77:6754–6758 (1980).

Jeffreys et al., "Individual-Specific 'Fingerprints' of Human DNA", *Nature,* 316:76–79 (1985).

Buroker et al., "A Hypervariable DNA Region on Human Chromosome 1p", *Genetics,* 113:PT2 (Supp. 1986).

Nakamura et al., "Characterization of Human 'Midisatellite' Sequence", *Nucleic Acids Research,* 15:2537–2547 (1987).

Litt et al., "A Highly Polymorphic Locus in Human DNA Revealed by Cosmid-Derived Probes", *Proc. Natl. Acad. Sci.,* 82:6206–6210 (1985).

Litt et al., "A Highly Polymorphic Locus in Human DNA Revealed by Probes from Cosmid 1–5 Maps to Chromosome 2g35→37", *Am. H. Hum. Genet.,* 38:288–296 (1986).

*Primary Examiner*—Amelia Burgess Yarbrough
*Assistant Examiner*—Ardin Marschel
*Attorney, Agent, or Firm*—Klarquist, Sparkman, Campbell, Leigh & Whinston

[57] ABSTRACT

A DNA probe which is homologous to at least a portion of a hypervariable DNA region D2S3 located at chromosome 2q35-37 in the human genome. The DNA region displays restriction fragment length polymorphism when digested with certain restriction endonucleases. The probe, p5-1-25, can be used to produce a genetic "fingerprint" to establish human identity, determine engraftment of bone marrow transplants, determine parentage, and otherwise map genes.

13 Claims, 1 Drawing Sheet

FIG. 1

DNA PROBE WHICH REVEALS A HYPERVARIABLE REGION ON HUMAN CHROMOSOME 2

This invention was made with government support under grant ROI-GM 32500 from the National Institutes of Health. The government has certain rights in the invention.

CROSS REFERENCE TO RELATED APPLICATION

This application is a continuation-in-part of copending U.S. patent application Ser. No. 46,831, filed May 4, 1987, and entitled "A DNA PROBE WHICH REVEALS A HYPERVARIABLE REGION ON HUMAN CHROMOSOME 1," and U.S. patent application Ser. No. 53,320, filed May 22, 1987, and entitled "A DNA PROBE WHICH REVEALS A HYPERVARIABLE REGION ON HUMAN CHROMOSOME 19."

BACKGROUND OF THE INVENTION

1. Field of the Invention

The present invention concerns a restriction enzyme mapping probe for human chromosome 2.

2. General Discussion of the Background

Restriction fragment length polymorphisms (RFLP) are useful markers for mapping the human genome, Borstein, et al., *Am. J. Hum. Genet.*, 32:314–331 (1980). As the number of known RFLPs increases, they are becoming ever more useful in the prenatal or early diagnosis of numerous hereditary diseases. RFLPs are also used in mapping a diseased gene to a specific chromosomal location, which may serve as the first step in cloning the gene.

Diseases that have been mapped by linkage studies with RFLPs include Huntington's Disease, Gusella, et al., *Nature*, 306:234–238, (1983); Duchenne's muscular dystrophy, Murray, et al., *Nature*, 300:542–544, (1982); X-Linked Retinitis Pigmentosa, Bhattacharya, *Nature*, 309:253–255 (1984); adult polycystic kidney disease, Reeders, et al., *Nature*, 317:542–544 (1985); and cystic fibrosis, Tsui, et al., *Science*, 230:1054–1056 (1985). RFLPs also have been crucial to the elucidation of mechanisms underlying hereditary cancer syndromes frequently associated with chromosome deletions such as retinoblastoma, Cavenee, *Nature*, 305:779–784 (1983), and Wilm's tumor, Koufos, et al., Nature, 309:170–172 (1984). In the future, RFLPs may be useful in characterizing the genetic contributions to susceptibility to common diseases which tend to cluster in families, such as colon cancer and schizophrenia, White, et al., *Nature* 13:101–105 (1985). For example, U.S. Pat. No. 4,623,619 discloses a method of using a probe to determine the liability of human individuals to develop atherosclerosis.

RFLPs can also provide individual-specific "fingerprints" of human DNA which can be used for such forensic purposes as identification of corpses, paternity testing, and identification of rapists. For example, Jeffreys, et al. disclosed in *Nature*, 316:76–79 (1985) that simple tandem-reptitive regions of DNA ("minisatellites") which are dispersed throughout the human genome frequently show substantial length polymorphism arising from unequal exchanges which alter the number of short tandem repeats in a minisatellite. The repeat elements in a subset of human minisatellites share a common 10-15 base-pair core sequence. A hybridization probe consisting of the core repeated in tandem can detect many highly polymorphic minisatellites simultaneously to provide a set of genetic markers of general use in human linkage analysis. Certain probes can detect sets of hypervariable minisatellites to produce somatically stable DNA "fingerprints" which are completely specific to an individual (or an identical twin) and can be applied directly to problems of human identification, including parenthood testing. Unfortunately, the Jeffreys, et al., probe detects repeated sequences that occur throughout the entire human genome, and give rise to very complex electrophoresis patterns that are sometimes difficult to interpret.

Hypervariable DNA regions have been reported near the human insulin gene (Bell, et al., *Nature*, 295:31–35 (1982)), in the α-globin gene cluster (Higgs, et al., *Nucleic Acids Res.*, 9:4213–4224 (1981); Proudfoot, et al., *Cell*, 31:553–563 (1982); Goodbourn, et al., *Proc. Natl. Acad. Sci. USA*, 80:5022–5026 (1983)), near the c-Ha-Ras-1 oncogene (Capon, et al., *Nature*, 302:33–37 (1983)) and at the telomere of the X and Y chromosomes (Cook, et al., *Nature*, 317, 687–692 (1985)). In all cases where DNA sequence information in these regions is available, it shows that the region consists of tandemly repeated sequences which vary in copy number among chromosomes. These hypervariable regions are hypothesized to arise by mitotic or meiotic unequal crossing over or by DNA slippage during replication (Jeffreys, et al., 1985). Hypervariable regions give rise to highly polymorphic loci at numerous genomic sites. DNA probes from such regions have been useful in paternity testing and other forensic applications as well as in human gene mapping.

It is therefore a primary object of this invention to provide a DNA probe which detects a hypervariable region of a human chromosome.

Another primary object is to provide such a probe which is specific to a single human chromosome.

Yet another primary object is to provide a probe which is easy to use and gives consistent results in forensic and medical tests.

SUMMARY OF THE INVENTION

The present invention is a DNA probe having a nucleotide sequence which is substantially identical or homologous to at least a portion of a hypervariable DNA region known as D2S3 located on chromosome 2 in the human genome. The DNA region displays a restriction fragment length polymorphism when digested with certain restriction endonucleases. Probe p5-1-25 is a particular probe homologous to this hypervariable region which reveals an invariant band at 4.2 kb and a multiple allele RFLP with at least 10 fragments varying in size from 2.0 to 2.9 kb when used to probe Southern blots of PstI-digested DNA's from unrelated individuals. Similar variation is seen with other enzymes, including TaqI.

The hypervariable DNA region to which probe p5-1-25 corresponds was identified by using a probe from a human genomic cosmid library. Cosmid 1-5 produced autoradiograms that indicated extensive DNA fragment size variation between unrelated individuals. Probe p5-1-25 is a subclone of the cosmid which has been placed in a plasmid for cloning.

The present invention includes a method of producing a genetic band pattern or "fingerprint" by digesting a human genome with a restriction endonuclease which, in combination with probe p5-1-25 that reveals D2S3, produces polymorphic fragments. The fragments are then separated by agarose gel electrophoresis, partially transferred to a nitrocellulose filter, and exposed to the radioactively labeled probe. The labeled probe hybridizes to fragments of DNA on the filter having homologous sequences. Autoradiographs produce a distinct band pattern which is used in human gene linkage analysis.

Probe p5-1-25 produces distinct band patterns which are characteristic of the individual from which the genome was taken. The band pattern can therefore be used for such forensic purposes as establishing the identity of a disfigured corpse or an accused assailant in a rape case. Medical applications include determining engraftment of bone marrow transplants, where it is helpful to determine if the marrow propagating in a patient's bone is diseased original tissue or healthy graft tissue. The probe can also be used to determine parentage because band patterns produced by the probes are inherited in a simple Mendelian fashion. Probe p5-1-25 is also useful in mapping genes because the probe marks a specific region of human chromosome 2 (2q35→37).

The foregoing and other objects, features, and advantages of the invention will become more apparent from the following detailed description of a preferred embodiment which proceeds with reference to the accompanying drawings.

DETAILED DESCRIPTION OF PREFERRED EMBODIMENT

Figure 1:
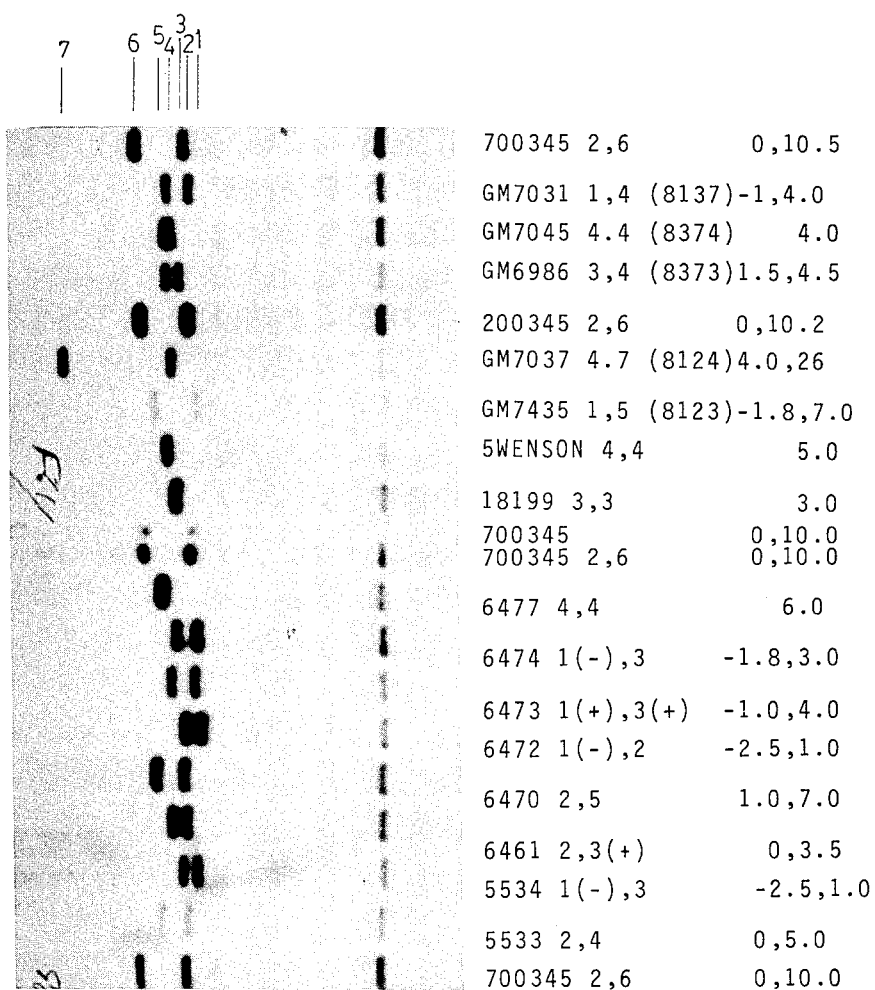
FIG. 1 shows Southern transfers of PstI digests of DNAs from 16 unrelated individuals probed with plasmid p5-1-25.

For the construction of linkage maps of human chromosomes, marker loci with multiple alleles and a polymorphism information content (PIC) near one are very useful. Botstein, et al., *Am. J. Human Genet.*, 32:314–331 (1980). Although several hundred RFLPs have been reported to date, only about 10 per cent have PIC values greater than 0.5. Willard, et al., *Cytogenet. Cell Genet.*, 40:360–490 (1985). The present inventor has addressed this problem of RFLP's having low PICs by using a method for rapidly screening cosmids and other repeat-containing DNA clones to identify those with inserts homologous to genomic regions especially rich in RFLPs. Litt and White, *Proc. Nat'l. Acad. Sci. USA*, 82:6206–6210 (1985).

Radioactively labeled probes were prehybridized with a vast excess of nonradioactive total human DNA under conditions which drive repetitive (but not single copy) DNA into duplex form. These probes were used directly on Southern blots of restricted DNAs from panels of unrelated individuals to visualize low and single copy bands. Probes that displayed multiple polymorphisms by this method were further studied to obtain single copy subclones which revealed RFLPs. The inventors have successfully used these methods to characterize a highly polymorphic locus on chromosome 2 and isolate probe p5-1-25 which is homologous to that region. A detailed description of these methods can be found in Litt and White, *Proc. Nat. Acad. Sci. USA*, 82:6206–6210 (1985); Bufton, et al., 19 *Am. J. Human Genet.*, 38:447–460; Bufton, et al., *Hum. Genet.*, 74:425–431 (1986); Buroker, et al., *Hum. Genet.*, 72:86–94 (1986); Litt et al., *Am. J. Hum. Genet.*, 38:288–296 (1986a); Litt, et al., *Hum. Genet.*, 73:340–345 (1986b)

Subclone p5-1-25, which was isolated from a random human cosmid (C1-5) using these methods, reveals an insertion/deletion polymorphism. The designation D2S3 has been assigned to this locus by the Committee on Human Gene Mapping by Recombinant DNA Techniques.

Other probes homologous to locus D2S3 were also isolated from cosmid C1-5, as described in Litt, et al., *Am. J. Hum. Genet.*, 8:288–296 (1986) which is incorported herein by reference. These probes, designated p5-1-30, p-5-1-32, and p-5-2-96, collectively reveal seven RFLPs. Ninety-three percent of 56 unrelated individuals studied were heterozygous for at least one of the seven RFLPs revealed by these three probes.

Methods of Preparing Cosmid and Subclones

Human DNA isolation, cosmid preparation and screening, subcloning, restriction mapping and hybridization procedures, somatic cell hybrid panels and in situ hybridization methods have been described in Litt and White, 1985; Bufton, et al., 1986; Buroker, et al., 1986; Litt, et al., 1986a; Litt, et al., 1986b); and Bufton, et al., 1987. Southern blots used in this study were hybridized at 45–47 and given a final wash in 0.IXSSC, 0.1 percent SDS at 65 . The somatic cell hybrid panel used in these studies has been previously described in Bufton, et al., 1986; Buroker, et al., 1986; and Litt, et al., 1986.

Human DNAs were prepared from leukocytes or transformed lymphoblasts (Bell et al., *Proc. Natl. Acad. Sci. USA*, 78:5759–5763 (1981)) with the addition of a second precipitation with ethanol in the presence of 2.5 M ammonium acetate.

Restriction enzymes were obtained from Promega Biotec (Madison, WI), New England Biolabs, and Bethesda Research Laboratories and were used according to the supplier's instructions. Human DNAs were digested with 5–10 units of enzyme per $\mu g$ of DNA and completeness of digestion was assessed by agarose gel electrophoresis of parallel digests containing $\lambda$ phage DNA in addition to human DNA. Barker et al., Cell, 36:131–138 (1984). Blot transfer hybridization was performed with nylon membranes (AMF Cuno, Meriden, CT) according to Barker et al., *Am. J. Hum. Genet.*, 36:1159–1171 (1985).

A partial library of human genomic DNA cloned in the cosmid vector KosI (Maniatis et al., *Molecular Cloning: A Laboratory Manual* (Cold Spring Harbor Laboratory, Cold Spring Harbor, NY), p. 50) was obtained from Ed Fritsch (The Genetics Institute, Boston). DNA was extracted from cosmids according to Ish-Horowicz and Burke (*Nucleic Acids Res.*, 9:2989–2998 (1981)) and was further purified by banding in CsCl/ethidium bromide gradients, treatment with RNase A, and centrifugation through 1 M NaCl.

Cosmids were screened for their utility in revealing multiple TaqI and/or MspI polymorphisms by a modification of the method of Ardeshir et al., *Mol. Cell. Biol.*, 3:2076–2088 (1983). Cosmids were nick-translated (Barker et al. (1984)) in the presence of $^{32}$P-labeled deoxynucleoside triphosphates (New England Nuclear) to give specific activities of at least $2 \times 10^8$ dpm/$\mu g$. After removal of unincorporated radioactivity by precipitation with spermine (Hoopes and McClure, *Nucleic Acids Res.*, 9:5493–5504 (1981)), cosmid probes were mixed with a vast excess of nonradioactive sonicated [average size, 500 base pairs (bp)] human placental DNA (Calbiochem), boiled, and prehydridized to a $C_0t$ of ca. 100 mol.sec/liter. Prehybridization was carried out in 0.12 M sodium phosphate, pH 7.0, at 65° C. for 5-6 hours. Prehybridized cosmid probes were hybridized with Southern blots made from TaqI or MspI digests of genomic DNAs from a panel of unrelated individuals, as described by Barker et al. (1984). Some probes that gave excessive lane background when hybridized at the usual temperature of 42.° C. were found to give satisfactory autoradiographs when hybridized at 55° C. Fisher et al., *Proc. Natl. Acad. Sci. USA,* 81:520-524 (1984). Blots were washed as described in Barker et al. (1984) with the addition of a high-stringency wash at 70° C. in 15 mM NaCl/1.5mM sodium citrate for 50 minutes.

Probe p5-1-25 is a 3.2 kb fragment subcloned into a plasmid. Sau3A digests of cosmid 1-5 were ligated into the BamHI site of the plasmid pJB-8. Ish-Horowicz and Burke (1981). The ligation mixture was used to transform *Escherichia coli* strain HBIOI. Transformants were selected on ampicillin plates and were screened by colony hybridization, using as probes total human DNA as well as appropriate restriction fragments of the cosmid.

Preparation and Characterization of RFLPs

Cosmid 1-5 was found during the course of screening random human cosmids for their ability to reveal PstI polymorphisms. As described above, the cosmid was used as a probe after prehybridization with a vast excess of human genomic DNA (Litt and White, 1985), and revealed multiple polymorphisms with the enzyme. Similar extensive variation was observed when the cosmid was used to probe Southern blots of DNAs digested with TaqI, which suggested that the polymorphisms were due to insertion/deletion events rather than to single-base changes affecting restriction sites.

As shown in FIG. 1, probe p5-1-25 reveals an invariant band at 4.2 kb and at least 10 alleles varying in size from 2.0 to 2.9 kb. A gel run for 24 hours shows less resolution than a PstI digest of the same genome run for 48 hours. The gel should preferably be run for 48 hours to produce a degree of resolution that facilitates interpretation of the band patterns. The allelic fragments detected by p5-1-25 are rather closely spaced, which makes long gel runs preferable.

The frequency of bands, in order of decreasing fragment lengths, was determined from a study of 53 unrelated European Caucasians. The frequencies are shown in Table 1:

TABLE 1

| Frequencies of Bands in Order of Decreasing Fragment Lengths | |
|---|---|
| Band | Frequency |
| A(1) | 0.057 |
| A(2) | 0.094 |
| A(3) | 0.094 |
| A(4) | 0.179 |
| A(5) | 0.038 |
| A(6) | 0.226 |
| A(7) | 0.236 |
| A(8) | 0.057 |
| A(9) | 0.009 |
| A(10) | 0.009 |

All bands show Mendelian inheritance with co-dominant segregation shown in informative IMR pedigrees 981 and 983.

Forty-one of fifty-three (77 percent) unrelated individuals tested were heterozygous.

The DNA fingerprints produced by probe p5-1-25 are sufficiently stable and individual-specific for use in human identification in, for example, forensic medicine. Badly disfigured corpses can be identified by preparing a genetic fingerprint with probe p5-1-25, and comparing the fingerprint to bands produced by DNA of a previously collected tissue sample from a known individual who is believed to be the corpse. If the band patterns match, identity has probably been established. Rapists can similarly be identified by comparing the band patterns from semen in the victim with the band patterns produced by the DNA of an individual suspected of committing the crime.

The simple Mendelian inheritance of band patterns produced by p5-1-25 makes it possible to use the probe in determining parentage, for example, in a disputed paternity suit. Approximately half of the polymorphic fragments in an offspring are derived from the father, and these paternal fragments can be identified by comparison of the mother's and offspring's DNA band patterns. All fragments present in the offspring but not in the mother must be present in the father (allowing for a possible rare new mutation). The probe produces at least 10 fragments, many of which are polymorphic. The large number of polymorphic fragments makes it possible not only to exclude paternity, if bands are present in the offspring but not the mother or putative father, but also to predict statistically the possibility of inclusion of paternity. The large number of polymorphic fragments produced by the probe provides a high statistical likelihood of inclusion of paternity.

Restriction Enzyme Mapping

Probes homologous to D2S3, such as probe p5-1-25, can also be used to map genes on chromosomes using the techniques disclosed by Gusella, et al. (1983), Murray, et al. (1982), Bhattacharya, et al. (1984), Reeders, et al. (1985) or Tsui, et al. (1985). A disease gene can be located by using the knowledge that a RFLP closely linked to a gene would be inherited with that gene. The inheritance of numerous RFLPs in families having the disease can be traced using random cloned DNA fragments from a human gene library as probes. An RFLP which is found to be inherited along with the disease indicates that the RFLP and disease gene are closely linked. Probes homologous to D2S3, such as probe p5-1-25, will therefore indicate the presence of a disease gene on human chromosome 2.

Homologous Probes

The present invention includes DNA probes having a base sequence substantially identical or homologous to at least a portion of locus D2S3. More particulary, the invention includes probes which contain a sequence substantially identical or homologous to the base pair sequence of probe p5-1-25. A substantially homologous sequence is one in which a high degree of homology between the sequences of two or more DNA molecules can be tested for by determining whether the DNA molecules in question hybridize to each other under stringent conditions, such as those set forth in Bethesda Research Laboratories, *DNA Detection System Instruction Manual* (Catalogue No. 8239SA), pp. 8-9 (1984). See also Leary et al., *Proc. Natl. Acad. Sci. U.S.A.,* 80:4045-4049 (1983), modifying the procedures of Wahl, et al., *Proc. Natl. Acad. Sci. USA,* 76:3683-3687 (1979).

Chromosomal Assignment

Chromosomal assignment of D2S3 was obtained using a panel of human x hamster and human x mouse somatic cell hybrids as described in Litt et al., *Am. J. Hum. Genet.*, 38:288-296 (1986). Molecular hybridization of EcoRI-digested DNA from these cell lines with DNA inserts from cosmid 1-5 showed that probes from this cosmid mapped to the long arm of chromosome 2. Additionally, in situ hybridization of [$^3$H]-labeled probes to metaphase chromosome preparations (Litt et al. (1986)) allowed more precise assignment of the locus to the region 2q35→37.

Probes p5-1-30, p5-1-32, and p5-2-96 were used to establish the chromosomal assignment of p5-1-25 to chromosome 2. Probes p5-1-30, p5-1-32, and p5-2-96 were isolated from the same cosmid CI-5 as p5-1-25 and would accordingly have the same genetic locus. The following data therefore illustrates that p5-1-25 is localized to chromosome 2q.

Eighteen cell lines were used as a mapping panel. The G35 cell lines are human-hamster hybrids derived from fusion of the Chinese hamster cell line E-36 with white blood cells (WBC) from a female carrier of the X/19W translocation t(X;19)(q23-25:.q13). Latt et al., *Chromosoma*, 57:135-153 (1976). The G17 and G24 cell lines are human-mouse hybrids derived from fusion of the mouse cell line RAG with WBC of the X/19W translocation carrier (G17 lines) or the X/19B translocation t(X;19)(qI::p13). Brook, et al., 19 *Hum. Genet.* All hybrid cell lines used were characterized by both isozyme and cytogenetic analysis. Burns et al., *Cytogenet. Cell Genet.*, 22:172-176 (1978). In addition, DNAs from all hybrids have also been analyzed with cloned DNA probes for all chromosomes except the Y.

DNAs were extracted from cell hybrids, digested with EcoRI, and subjected to blot-transfer hybridization as described in Litt et al., *Cytogenet. Cell Genet.*, 37:210-273 (1984). Blots were probed with nick-translated inserts from subclones of cosmid 1-5. The three subclones used, p5-1-30, p5-1-32, and p5-2-96, each reveal RFLPs when used as probes against Southern transfers of appropriately digested genomic DNAs from panels of unrelated individuals.

Subclone p5-2-96 was labeled by nick-translation according to the method of Harper and Saunders to specific activity of $4 \times 10^7$ dpm/vg using [$^3$H]TTP (65 Ci/mmol) and [$^3$H]dCTP (60 Ci/mmol, Amersham, Arlington Heights, Ill.). In situ hybridization to metaphase spreads from normal male cells was performed according to Harper and Saunders, *Chromosoma*, 83:431-439 (1981). Probe p5-2-96 was diluted to a final concentration of 50 ng/ml in pH 7.0 hybridization buffer that contained 50 percent formamide, 2 X SSCP, 10 percent dextran sulfate, and 50 µg/ml salmon sperm DNA. Chromosomes were hybridized for 12 hours at 37°C.; excess probe was then removed by washing three times for 2 minutes each time, in 2 X SSC, 50 percent formamide at 37°C. Following dehydration with an alcohol series, Kodak NTB-2 liquid emulsion was applied to the slides for a 5-day exposure. Slides were developed and were R-banded using a modification of the technique of Schweizer, *Cytogenet. Cell Genet.*, 27:190-193 (1980). For photographs illustrating grain distribution, preparations were destained and restained with Wright's stain.

EcoRI digests of DNAs from parental mouse and hamster cells and from 16 human-rodent hydrid cell lines were probed with [$^{32}$P]-labeled inserts from subclones p5-1-30, p5-1-32, and p5-2-96 (FIG. 2). FIG. 2 shows Southern blots of EcoRI digests of DNAs from parental and hybrid cell lines probed with the inserts from sublcones p5-1-30(A), p5-1-32(B), and p5-2-96(C). The leftmost lane of each blot contains size standards. Eighteen cell lines were used as a mapping panel. The G35 cell lines are human-hamster hybrids derived from fusion of the Chinese hamster cell line E-36 with white blood cells (WBC) from a female carrier of the X/19W translocation t(X;19)(q23-25::q13). The G17 and G24 cell lines are human-mouse hybrids derived from fusion of the mouse cell line RAG with WBC of the X/19W translocation carrier (G19 lines) or the X/19B translocation t(X;19)(q1::p13). All hybrid cell lines used were characterized by both isozyme and cytogenetic analysis. In addition, DNAs from all hybrids have also been analyzed with cloned DNA probes for all chromosomes except the Y.

Subclone p5-1-30 did not cross hybridize with the rodent parental cell line DNAs and gave hybridization signals only with hybrid cell lines G35D5, G35F3, and G24A9 (panel A). Subclone p5-1-32 gave hybridization signals at 8.3 and 5.9 kilobases (kb) only with these same three hybrid cell lines (panel B). The nature of the low molecular weight bands seen at the bottom of panel B for cell lines E36, G35E3, G35C4, and G35C5 was unexplained. However, since this band is present in the E36 hamster parental cell line, it is unlikely to have arisen from specific hybridization of probe p5-1-32 to a human genomic sequence. As shown in Table 2, the results given by probes p5-1-30 and p5-1-32 are completely concordant with the presence of the entire chromosome 2. Cell line G35D3, which is positive for human MDHI (a marker for 2p23 and which lacked human IDHI (a marker for 2q32→qter) failed to give a hybridization signal with probes p5-1-30 and p5-1-32. Results identical to those seen with G35D3 were also seen with cell line G24A4C, another hybrid cell line that was MDHI positive and IDHI negative (data not shown).

FIG. IC shows that, when probed with p5-2-96, only cell lines G35D5, G35F3, and G24A9 gave signals at 6.7 kb, consistent with the localization of this probe on chromosome 2q, as seen for the other two subclones. A signal at 7.6 kb that is weaker by approximately 10-fold than the 6.7-kb signal was observed with cell lines G35A2, G35C2, G35F5, G35D3, G35A4, G35E4, G175, and G24A9. As can be seen by inspection of Table 2, these weak 7.6-kb signals are completely concordant only with the presence of chromosome 4. Other cell lines (G35D2, G35E3, G35C4, G35B5, G35C5, and G35B4) as well as the hamster parent E36, which lacked human chromosome 4, also gave signals at about 7.6 kb, but these signals were much weaker than those given by the cell lines containing chromosome 4. Photographs of ethidium bromide-stained gels used to make the blot shown in FIG. 2 of Litt, et al., *Am. J. Hum. Genet.*, 38:292 (1986), indicate that approximately equal amounts of total DNA were loaded 1are each lane. Hence, the extremely weak signals given by this latter group of cell lines can be attributed to cross reaction of probe p5-2-96 with a segment of hamster parental DNA. Also, the very weak signals at about 5 kb in the mouse parent RAG as well as the mouse-human hybrid cell line G175 can be attributed to similar cross reaction with a segment of mouse parental DNA.

TABLE 2

Chromosome Contents of Hybrid Cell Lines

| Cell Line | 1 | 2p | 2q | 3 | 4 | 5 | 6 | 7 | 8 | 9 | 10 | 11 | 12 | 13 | 14 |
|---|---|---|---|---|---|---|---|---|---|---|---|---|---|---|---|
| G35D5 | + | + | + | + | − | − | + | + | − | − | + | − | − | + | + |
| G35F3 | − | + | + | + | − | + | − | + | + | − | + | + | + | − | − |
| G35D2 | ± | − | − | − | − | + | + | − | − | + | − | + | + | − | − |
| G35E3 | − | − | − | − | − | + | + | − | + | − | − | + | + | + | + |
| G35A2 | − | − | − | + | + | − | + | − | − | − | − | + | − | − | + |
| G35C2 | − | − | − | − | + | − | − | − | + | − | − | R | − | − | + |
| G35C4 | − | − | − | − | − | + | + | − | − | R | − | − | + | − | + |
| G35B5 | − | − | − | − | − | − | p | + | − | − | − | + | p | + | − |
| G35F5 | ± | − | − | + | + | − | + | − | − | + | − | + | − | + | + |
| G35D3 | − | + | − | − | + | − | − | + | + | + | + | − | − | − | ± |
| G35C5 | − | − | − | p | − | + | − | + | + | + | + | − | p | − | − |
| G35A4 | + | − | − | + | + | − | + | − | + | + | − | − | − | − | + |
| G35B4 | + | − | − | − | − | + | − | − | − | − | + | + | + | − | − |
| G35E4 | − | − | − | − | R | − | − | − | − | R | + | − | − | − | − |
| G175 | ± | − | − | − | + | − | + | − | + | − | + | − | − | + | + |
| G24A9 | − | + | + | − | + | − | + | − | + | + | + | − | − | ± | + |
| Discordancy fraction | 4/14 | 1/16 | 0/16 | 4/15 | 8/15 | 7/16 | 7/15 | 4/16 | 7/16 | 7/14 | 4/16 | 8/15 | 6/14 | 5/15 | 8/15 |

| Cell Line | 15 | 16 | 17 | 18 | 19 | 20 | 21 | 22 | X | Y | Scoring M |
|---|---|---|---|---|---|---|---|---|---|---|---|
| G35D5 | + | + | + | + | + | + | − | + | a | − | + |
| G35F3 | − | + | − | + | + | + | − | − | a | − | + |
| G35D2 | + | + | − | + | + | + | − | + | a | − | − |
| G35E3 | − | + | − | + | + | + | + | + | a | − | − |
| G35A2 | − | − | − | − | + | + | + | + | + | − | − |
| G35C2 | − | + | − | − | R | − | − | − | + | − | − |
| G35C4 | − | − | − | ± | + | + | + | − | a | − | − |
| G35B5 | − | − | + | − | + | + | − | − | a | − | − |
| G35F5 | − | + | + | + | + | ± | + | + | + | − | − |
| G35D3 | − | + | + | − | + | + | + | + | a | − | − |
| G35C5 | + | + | + | − | + | + | + | + | a | − | − |
| G35A4 | − | + | − | − | + | + | + | − | + | − | − |
| G35B4 | − | − | − | + | + | − | − | + | + | − | − |
| G35E4 | + | − | − | − | + | − | − | − | a | − | − |
| G175 | + | − | − | − | + | − | − | + | a | − | − |
| G24A9 | + | − | − | ± | + | + | + | − | q | − | + |
| Discordancy fraction | 5/16 | 8/16 | 6/16 | 4/14 | 12/15 | 8/15 | 9/16 | 10/16 | 13/16* | 3/16 | |

*Discordancy fractions with Xq24-qter and Xpter-q24 are 13/16 and 5/5, respectively.

Explanation of Table 2

The designations are: (+) presence or (−) absence of a human chromosome: R, rearranged chromosome as determined by disruption of a syntenic group or by a cytogenetic abnormality; ± chromosome present in less than 15 percent of cells and/or the isozyme or DNA probe characteristic of the chromosome weakly positive. For calculation of the discordancy fractions, hybrids with a rearranged chromosome or those where the chromosome was present in less than 15 percent of the cells were excluded from analysis. The isozymes MDH-1 and IDH-1 were used to monitor the segregation chromosomes 2p and 2q, respectively. Hybrids designated as +for both 2p and 2q had a normal appearing chromosome 2 by cytogenetic analysis. The discordancy fractions for the chromosome 4 component of probe p5-2-96 ranged from 0.20 to 0.96 (not shown). The segregation of chromosome 4 was monitored with a DNA probe for human serum albumin, Kurnit et al., Cytogenet. Cell Genet., 34:282–288 (1984), The isozyme PGM-2, Bootsma and Kidd, Cytogenet. Cell Genet., 37:22–46 (1984), and by cytogenetic techniques. The column designated M indicates the presence or absence of the 8.0, 8.3, and 5.9 and 6.7-kb EcoRI fragments in Southern transfers probed with subclones p5-1-30, p5-1-32, and p5-2-96, respectively.

In Situ Hybridization

A representative, sequentially stained metaphase spread from the in situ hybridization studies is shown in FIG. 3 of Litt, et al., Am. J. Hum. Genet., 38:294 (1986). The silver grains revealing hybridization of the probe are observed with standard staining, and the particular chromosomes to which the probe has hybridized are identified by their fluorescent R-banding pattern. FIG. 4 of Litt, et al., Am. J. Hum. Genet., 38:295 (1986), summarizes the results of scoring 100 cells from a normal male. Each dot in the histogram represents a silver grain observed over a specific chromosomal region. Nineteen of the 100 cells had a grain localized to the region 2q35→37; the remainder of the grains were randomly distributed over the chromosomes.

The somatic cell hybrid panel results indicate that the insert of cosmid 1-5 is homologous to a DNA segment on chromosome 2 and that this segment is probably on the long arm. Subclone p5-2-96 of the cosmid also hybridizes weakly with a DNA segment on chromosome 4. Localization of the cosmid insert to the long arm of chromosome 2 is confirmed by the results from in situ hybridization studies, which assign this highly polymorphic locus to 2q35→37.

D2S3 may be regarded as a single marker locus useful for mapping genes on the long arm of human chromosome 2. Because probes p5-1-25, p5-1-30, p5-1-32, and p5-2-96 hybridize strongly and specifically in situ to 2q35→37, they will be useful in cytogenetic applications, such as rapid detection of translocations involving this region, using biotin-labeled probe and fluorescence microscopy. Pinkel, et al., *Nat. Acad. Sci. USA*, 83:2934-2938 (1986). The highly polymorphic nature of the hypervariable region also makes the probes potentially useful tools for following engraftment of donor bone marrow after transplanation (Blazar, et al., *Blood*, 66:1436-1444 (1985)), and for paternity testing and other forensic applications. Furthermore, an oligomer probe might be useful in isolating genomic clones capable of revealing additional hypervariable regions.

ATCC Deposit

Probe p5-1-25 has been deposited with American Type Culture Collection in Rockville, Maryland, and assigned ATCC accession No. 40328. The deposited probe is a plasmid containing the subclone p5-1-25. In use, the probe would be amplified through bacterial transformation to produce a bacterial colony. The plasmid would then be isoloated and labeled, for example, with radioactive phosphorous.

Having illustrated and described the principles of the invention in a preferred embodiment, it should be apparent to those skilled in the art that the invention can be modified in arrangement and detail without departing from such principles. I claim all modifications coming within the spirit and scope of the following claims.

I claim:

1. A plasmid having ATCC accession No. 40328 which contains a clone of DNA probe p5-1-25.

2. A DNA probe containing a sequence of the a plasmid having ATCC accession No. 40328, which insert hybridizes to locus D2S3 of the human genome.

3. The probe of claim 2 that is a plasmid.

4. The probe of claim 2 further comprising a label which enables detection of the probe.

5. A recombinant DNA molecule comprising a DNA segment containing a sequence from the base sequence of probe p5-1-25, and a label for detecting the sequence.

6. The molecule of claim 5 that is a plasmid.

7. A DNA probe containing the DNA sequence of a subclone p5-1-25.

8. The probe of claim 4 wherein the label is a radioactive material.

9. The probe of claim 8 wherein the radioactive material is phosphorous.

10. The probe of claim 5 wherein the label is a radioactive material.

11. A DNA probe having a nucleotide sequence which hybridizes to at least a portion of locus D2S3 of chromosome 2 in the human genome.

12. The DNA probe of claim 11 wherein the nucleotide sequence is identical to at least a portion of locus D2S3.

13. A DNA probe which hybridizes to a hypervariable region of the human genome at locus D2S3 and reveals an invariant band at 4.2 kb and a multiple allele RFLP with at least 10 fragments varying in size from 2.0 to 2.9 kb when used to probe Southern blots of PstI-digested DNA.

* * * * *